United States Patent
Vdovjak

(10) Patent No.: US 9,892,231 B2
(45) Date of Patent: Feb. 13, 2018

(54) AUTOMATED ASSERTION REUSE FOR IMPROVED RECORD LINKAGE IN DISTRIBUTED AND AUTONOMOUS HEALTHCARE ENVIRONMENTS WITH HETEROGENEOUS TRUST MODELS

(75) Inventor: Richard Vdovjak, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1411 days.

(21) Appl. No.: 13/132,949

(22) PCT Filed: Nov. 19, 2009

(86) PCT No.: PCT/IB2009/055183
§ 371 (c)(1),
(2), (4) Date: Jun. 6, 2011

(87) PCT Pub. No.: WO2010/067229
PCT Pub. Date: Jun. 17, 2010

(65) Prior Publication Data
US 2011/0246237 A1   Oct. 6, 2011

Related U.S. Application Data

(60) Provisional application No. 61/121,985, filed on Dec. 12, 2008.

(51) Int. Cl.
*G06F 19/00* (2011.01)
*G06Q 50/22* (2012.01)
*G06Q 50/24* (2012.01)

(52) U.S. Cl.
CPC ........... *G06F 19/322* (2013.01); *G06Q 50/22* (2013.01); *G06Q 50/24* (2013.01)

(58) Field of Classification Search
USPC .......................................................... 705/2, 3
See application file for complete search history.

(56) References Cited

U.S. PATENT DOCUMENTS 6,912,549 B2    6/2005   Rotter et al.
7,028,049 B1    4/2006   Shelton
(Continued)

FOREIGN PATENT DOCUMENTS

JP    2008117220 A    5/2008
JP    2008204378 A    9/2008
(Continued)

OTHER PUBLICATIONS

Gummadi, A.; Yoon, J.P.; "Modeling group trust for peer-to-peer access control," Proceedings of the 15th International Workshop on Database and Expert Systems Applications (DEXA'04) pp. 971-978, Aug. 30-Sep. 3, 2004.*

(Continued)

*Primary Examiner* — Victoria P Shumate
*Assistant Examiner* — Jonathan Durant

(57) ABSTRACT

An assertion acceptance value matrix (300) indicates the reliability of assertions, particularly assertions or decisions whether records match or do not match, made by other medical institutions in a federation of medical institutions with different patient record systems and some common patients. Records from different institutions with a high likelihood of matching or not matching are automatically matched or not matched. Those that are ambiguous are manually reviewed. The assertion acceptance value matrix is used to reduce or expedite the manual review.

19 Claims, 4 Drawing Sheets

(56) References Cited

U.S. PATENT DOCUMENTS

| | | |
|---|---|---|
| 7,167,858 B2 | 1/2007 | Naeymi-Rad et al. |
| 2003/0120652 A1 | 6/2003 | Tifft |
| 2003/0126102 A1* | 7/2003 | Borthwick .................. 706/21 |
| 2004/0044542 A1 | 3/2004 | Beniaminy et al. |
| 2005/0246205 A1 | 11/2005 | Wang et al. |
| 2006/0287890 A1 | 12/2006 | Stead et al. |
| 2008/0115193 A1 | 5/2008 | Prax et al. |

FOREIGN PATENT DOCUMENTS

| | | |
|---|---|---|
| WO | 0122285 A2 | 3/2001 |
| WO | 03021485 A2 | 3/2003 |

OTHER PUBLICATIONS

Gummadi, A. et al., "Modeling group trust for peer-to-peer access control," Proceedings of the 15th International Workshop on Database and Expert Systems Applications (DEXA'04) pp. 971-978, Aug. 30-Sep. 3, 2004.

* cited by examiner

AUTOMATED ASSERTION REUSE FOR IMPROVED RECORD LINKAGE IN DISTRIBUTED AND AUTONOMOUS HEALTHCARE ENVIRONMENTS WITH HETEROGENEOUS TRUST MODELS

The present application relates to the art of data continuity. It finds particular application to the management of patient records in a medical environment. However, it will also find use in other types of applications in which data continuity is of interest.

It is common for patients to receive care from multiple healthcare providers which are geographically dispersed at multiple sites. Using multiple healthcare providers results in a patient receiving multiple patient identifiers, each patient identifier local to a specific healthcare provider. Patient data such as medical images and other relevant medical information is spread across multiple healthcare provider sites. In order for a healthcare provider to retrieve patient data records stored among multiple healthcare provider sites, it is necessary to reconcile the multiple patient identifiers of the corresponding healthcare providers and to link the multiple patient identifiers together. There is currently a need for a system that enables medical records to follow the patient as the patient moves between multiple healthcare providers which are dispersed geographically at multiple sites.

The present application provides an improved method and apparatus which overcomes the above-referenced problems and others.

In accordance with one aspect, a method is presented of reusing comparisons, comprising receiving a record supplied by an outside party, comparing the received record with a plurality of records currently maintained by a receiving party in order to determine if any two compared records correspond to a same customer. This is used in generating a likelihood ratio based on a probability that the compared records match; and this ration is used in comparing the likelihood ratio to an accept threshold and to a reject threshold, the accept threshold being different from the reject threshold. Then; assigning a record to an exception list when the record's likelihood ratio a value is both less than the accept threshold and is also greater than the reject threshold to an exception list. Then determining whether the records on the exception list should be accepted as a match or rejected as not matching and recording the determination; receiving assertions made by outside parties whether records on the exception list were accepted or rejected as matching. Then; comparing the records on the exception list that were at least one of accepted and rejected by both the party receiving the record and each outside party in order to calculate an assertion acceptance value for each outside party. Finally, recording the assertion acceptance values in a matrix format is performed.

In accordance with another aspect, an apparatus is presented for generating reusable comparisons, comprising of an input which receives a record supplied by an outside party; a database which stores a plurality of records; at least one processor which compares the received record with each record retrieved from the database in order to generate a likelihood ratio based on a probability that the compared records match. Then the apparatus compares the likelihood ratio to both an accept threshold and a reject threshold, assigns a record that is between the accept threshold and the reject threshold to an exception list for a manual determination whether the records on the exception list match. The at least one processor further receives assertions made by at least one outside party wherein the assertion comprises whether the records on the exception list were accepted or rejected as matching; compares the records on the exception list that were at least one of accepted and rejected both by the party receiving the record and each outside party in order to calculate an assertion acceptance value for each outside party. Finally, the apparatus records the assertion acceptance values in a matrix format.

In accordance with a further aspect, a method is proposed of matching patient records for a plurality of medical institutions with different medical records systems, with some patients having records in a plurality of the medical records systems. The method comprises comparing a selected patient medical record in a medical records system with a plurality of patient records from at least one other medical record system, generating likelihood ratios indicative of a probability that the selected patient medical record matches each of the compared records. The method engages in automatically matching the selected patient medical record with one of the compared records if the likelihood ratio exceeds an accept threshold, not matching the selected patient medical record with compared records that meet a reject threshold, and if the selected patient medical record and one or more compared records do not meet either the accept or the reject threshold, assigning the selected patient medical record to an exception list for manual review. Then receiving an indication whether the selected patient medical record was matched to one of the compared records by another of the medical institutions; and finally performing at least one of the manual review and the generating step in accordance with an assertion acceptance value matrix indicative of a reliability of matches made by other medical institutions.

An advantage resides in the ability to reduce the need to continually evaluate the same record a plurality of times.

Another advantage resides in a greater assurance of accuracy.

Another advantage resides in identifying inconsistent results and potential errors.

An advantage resides in the fact that other healthcare providers can see how a specific healthcare provider evaluated the medical records of a particular patient at a previous healthcare provider and use this evaluation to make their own assessment of that specific patient's medical records.

The invention may take form in various components and arrangements of components, and in various steps and arrangements of steps. The drawings are only for purposes of illustrating the preferred embodiments and are not to be construed as limiting the invention.

Figure 1:
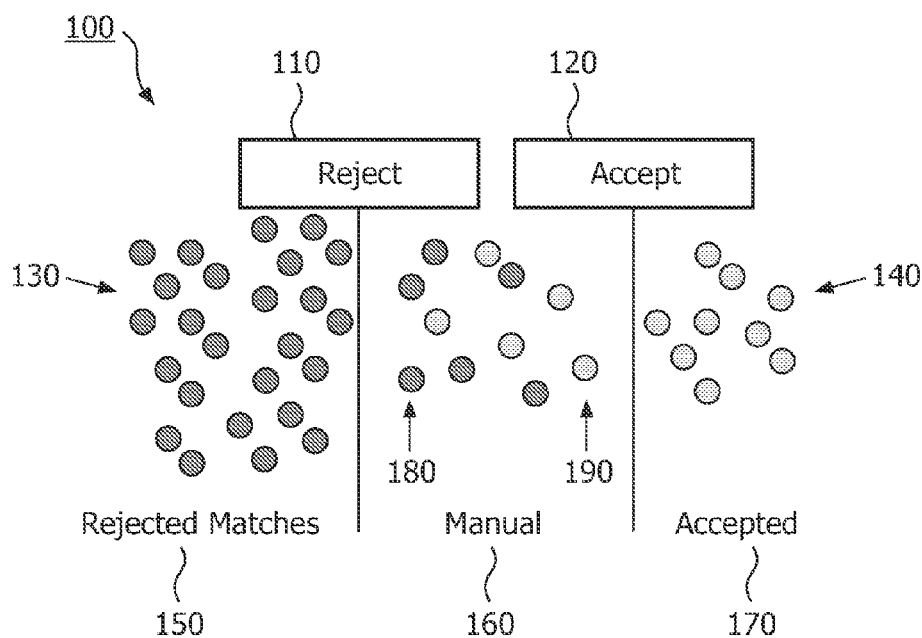
FIG. 1 illustrates two thresholds for distinguishing three outcomes with respect to record matching.

With reference to FIG. 1, a probabilistic algorithm, which compares a fixed record with a number of candidates for a match, computes for each candidate a likelihood ratio or weighted score that is individually compared with reject 110 or accept 120 thresholds. The reject threshold 110 is used as a basis for a comparison used to decide whether the record falls below the reject threshold 110. If the likelihood ratio of a record is less than the reject threshold 110 the record is rejected 130 as not being a match 150 and the record is not linked The accept threshold 120 is used as a basis for a comparison used to decide which records exceed the accept threshold. If the likelihood ratio of a record is greater than the accept threshold 120, then the record 140 is accepted as a match 170 and the record is linked. If the record is greater than the reject threshold 110 and also less than the accept threshold 120, then the computed likelihood falls between the accept and the reject thresholds. Here, the record might be either rejected 180 or accepted 190. The decision is not made automatically, but rather is flagged for a manual review 160 by qualified personnel. The manual review is made to determine if the record should be properly rejected 180 or accepted 190 as a match. The manual review 160 of uncertain matches is of crucial importance in order to minimize linkage errors, as such errors can have far-reaching consequences ultimately endangering patient health.

As medical providers or health systems associate or consolidate, it becomes advantageous to share patient records. The same patient may exist in multiple provider databases with different medical record numbers (MRN). The flow of information into and out of the patient record is typically channeled through a Master Patient Index (MPI) that associates a unique medical record number (MRN) in the provider's numbering system to each patient entity when a unit record exists. To obtain an enterprise-wide view on the patients across distributed data sources, an enterprise master patient index (EMPI) is implemented with one common, enterprise wide unique MRN for each patient such that each patient is known by one and only one MRN, independent of the specific medical facility such that the same one patient will have the same unique MRN at each and every medical provider participating in the present application disclosed system. The EMPI is developed through integration of the individual MPIs of the entities which together make up the enterprise. Generally, the integration is achieved by comparing demographic attributes, such as first and last name, gender, date of birth, address, and other demographic data to create the EMPI as a form of an enterprise-level patient identifier where one single unique MRN would identify the same patient at every medical facility using the present system. Such an enterprise level patient identifier is rarely based on a single identifier shared across the different organizations in the enterprise.

Probabilistic algorithms can be used to compare a fixed record with a number of candidates for a match, computing for each candidate a likelihood ratio or weighted score that is compared to the chosen accept and reject thresholds as explained above in connection with FIG. 1. This method is used to decide whether or not to link the records to a common identifier or enterprise-wide MRN. When the decision cannot be taken automatically such as when the computed likelihood falls below the two thresholds, qualified personnel review or flag the potential matches before they are accepted and also review the mismatches before they are rejected. The manual review of uncertain matches is very important in order to minimize linkage errors, but at the same time it is time-consuming and expensive.

Figure 2:
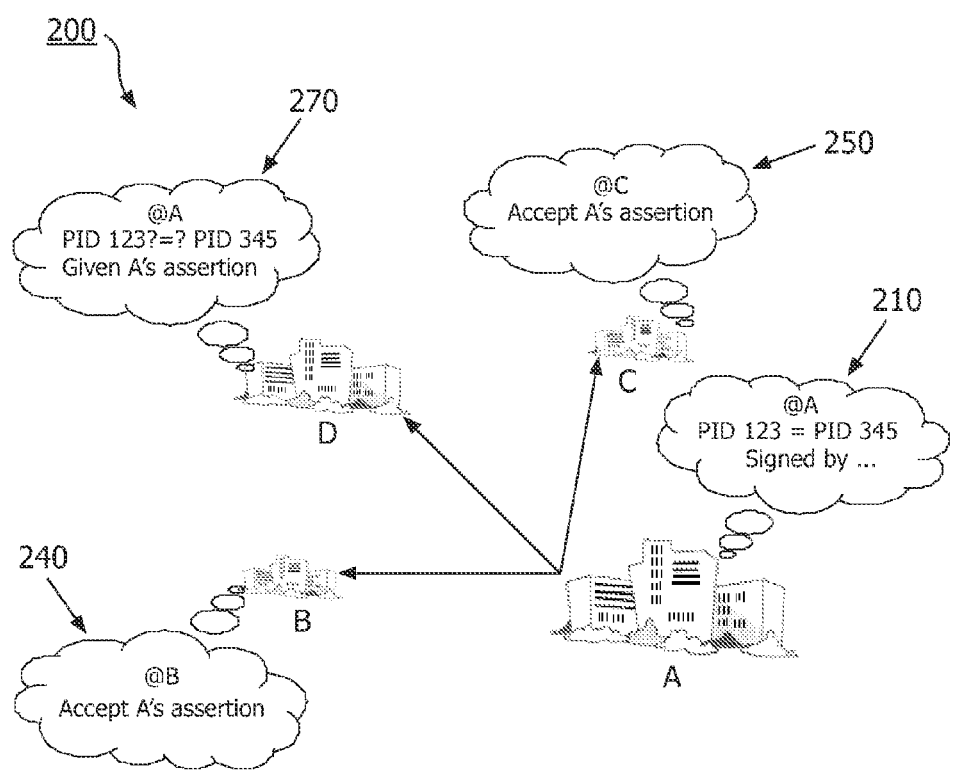
FIG. 2 illustrates the assertion acceptance in distributed heterogeneous environments with autonomous sites.

With reference to FIG. 2, an assertion-based record linkage which provides a link between records at two different medical providers that have a likelihood of pertaining to the same patient, allows for keeping track of assertions throughout the group of institutions also referred to as a federation or enterprise, treating all of the assertions as local ground truth for the institutions that issued them but not necessarily for other institutions. An assertion is a belief that two medical records do o do not refer to the same patient. The customer is assigned a unique record number to a customer's records. The customer's demographic data is compared with the demographics data of each record in a collection of records that are potentially belonging to the same customer, to derive a likelihood ratio for each compared record. Each likelihood ratio is compared to a defined accept threshold and to a defined reject threshold. During the manual review of the records falling between the two thresholds, an assertion is made about the pair of records to be matched, based on the likelihood ratio comparison, stating whether it is believed that the two records belong to the same patient or not The local ground truth approach requires all participating institutions to make their own manual review of a record in order to resolve the exception list of records that needed to be manually reviewed. When the trust level within the group of institutions or federations is low, each institution does not take assertions of other institutions as granted. The worst case scenario in which no institution trusts any other institution is the most time-consuming to solve.

The trust level among some of the participating institutions can be large. For instance, imagine a large well-established healthcare provider 200 which may have acquired some smaller institutions with their own patient identification schemes. Let us assume that hospital A, hospital B, and hospital C, participate together in one federation which is expanded to add another institution such as D. Over time, hospitals A, B, and C have established common procedure and come to have complete confidence in each other. In this example, when hospital A makes an assertion 210 about two participating identifiers being the same, this assertion would be accepted as local truth not only as hospital A, but also hospital B, and hospital C. In such situation, there is no need for a manual review of hospital B and hospital C. Hospital D on the other hand may not have developed such a high level of confidence and is able to locally override hospital A's assertion. At the same time, the assertion produced by hospital A could play a role in the automated matching process that determines the cases for manual review of hospital D. Of course the influence of hospital A's assertion with respect to hospital D's matching will be larger or smaller depending on the level of trust hospital D has toward hospital A. Assertions 240, 250, and 270 made by hospitals B, C, and D, respectively, are treated analogously.

Figure 3:
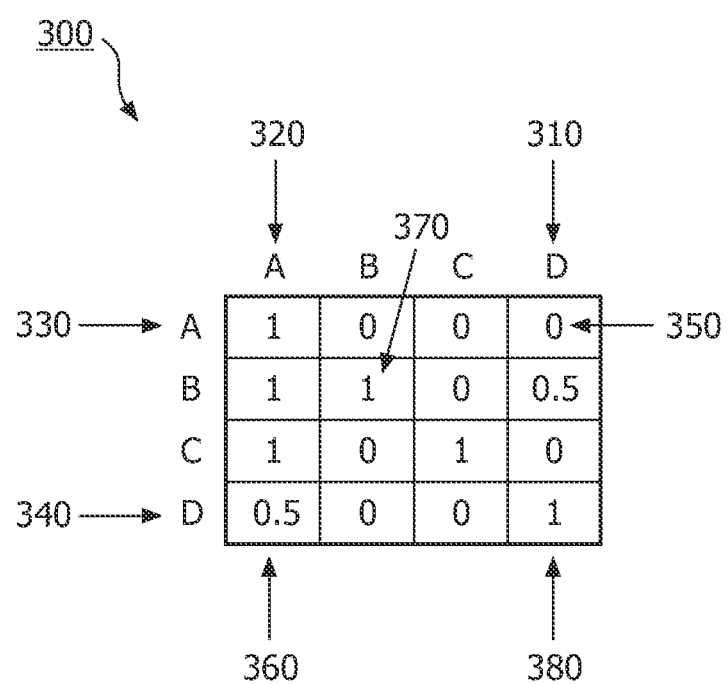
FIG. 3 illustrates an assertion acceptance matrix for a federation with four participating institutions. Note that the matrix data structure is just one of many possible way to store this information other approaches (e.g. a list of lists, set of dictionaries etc.) may be equally applicable.

The present application proposes to describe a means for explicitly quantifying a mutual trust pair wise among all participating institutions within the federation of institutions, and to use this data to maximize re-use of available assertions in the manual review phase, thus minimizing the labor intensive task of performing the assertion each time determination process the patient record is accessed, while allowing for a heterogeneous trust model within the federation. To this end, a federation trust matrix is created and applied to automated assertion re-use, where the available assertions become a part of the probabilistic formula that computes the thresholds. This approach allows for a smooth and efficient assertion handling facilitating the re-use of assertions in the automated patient identification process within collaborating heterogeneous healthcare environments. With reference to FIG. 3, to allow for assertion re-use in the context of heterogeneous healthcare multi-enterprise patient matching, we propose the use of a so-called acceptance matrix 300, which explicates the level of assertion acceptance among the participating institutions. The rows 330 in the exemplary matrix 300 represent the institutions that receive the assertions; the columns 310 represent the institutions that issue the assertions. The values range from 0 to 1 (e.g., 0% to 100%) and indicate the percentage or weight which the receiving institution assigns to the assertion of an institution, where 0 means no acceptance 350, and 1 means treating the incoming assertion as ground truth 370.

In a variation the assertion matrix 300, the acceptance percentage comprising the weight of positive and negative assertions, can be different with respect to assertions from one issuing institution about a patient ID match and mismatch respectively; each cell in the matrix variation would contain two acceptance values, one for the positive assertion and one for the negative assertion. Here, a cell would contain two values, one value being the acceptance rate as a probability of a record being accepted with 0 being no acceptance or rejection and 1 being certain acceptance; while the second value would be a probability of being rejected, with 0 being no acceptance and a 1 being a certain rejection. These two values would reside in the same cell of a matrix, either side by side, above and below, one on top of another, diagonally adjacent from each other, or any number of combinations or in parallel matrices, or can also be stored in another appropriate type of data structure e.g. list of lists etc.

It is noted that the matrix 300 has ones in diagonal matrix cells, indicating that institutions take their own assertion as ground facts 380. However, each institution may recognize the possibility of error and give itself a high percent or weight, e.g., 0.95, but may not accept it as a ground fact. Also note that the matrix 300, or variations thereof, do not have to be symmetric as the trust degree is not necessarily symmetric either, such as when hospital D accepts an assertion from hospital A with the degree of 0.5 (360), but hospital A does not take hospital D's assertion into account at all (no acceptance 350). The value from the assertion matrix 300 can be embedded into the automated matching algorithm that is adopted, by simply increasing the acceptance changes with the indicated percentage, or embedding this percentage in a chosen probabilistic formula, next to other usual matching criteria such as a match based on a last name, date of birth, and the like. So for instance in a case of hospital D, it will increase the likelihood of a patient ID match by 50% if hospital D receives an assertion from hospital A about a particular case. After hospital D receives hospital A's assertion, it then proceeds with the matching algorithm computing the overall matching score taking into account all available demographic data plus the increased likelihood based on hospital A's assertion. Based on the score of the chosen threshold, the patient IDs are then automatically linked or proclaimed as different or put for a manual review.

The problem of patient identity in a federated environment in the absence of a global common identifier is one of the key issues that need to be solved as a prerequisite to being able to build and deploy a Federated Picture Archiving and Communication System (PACS) solution. The present application addresses the manual review phase of the matching process in the context of autonomous environments.

Figure 4:
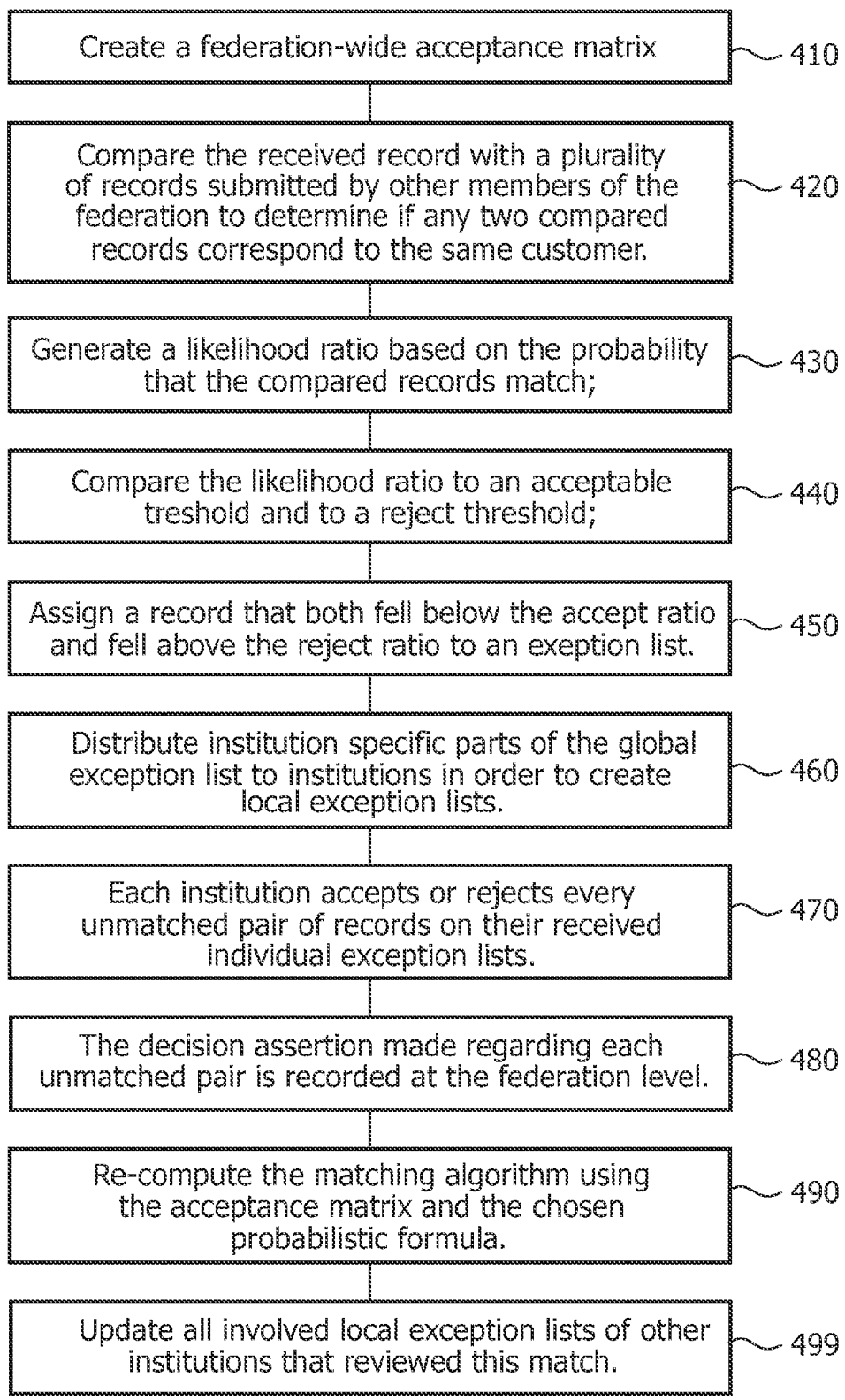
FIG. 4 illustrates a flow chart of the method claim.

With reference to FIG. 4, a flow chart of the method steps is presented. First a record supplied by an outside party is received 410. This record is then compared with a plurality of records 420 currently maintained by the receiving party in order to determine if any two compared records correspond to the same customer. From this comparison, a likelihood ratio is generated 430 based on the probability that the compared records match. This likelihood ratio is then compared 440 with both an acceptable threshold and a reject threshold. Any record with a likelihood ratio that is both less than the accept ratio and greater than the reject ratio 450 is placed on an exception list for manual review. The records on the exception list are individually evaluated manually 460 in order to determine if these records should be accepted or rejected and this determination is recorded. Then the total number of records evaluated, accepted and rejected is segmented by an outside party in order to calculate an acceptance ratio for each individual outside party 470. This acceptance ratio data is then placed 48 in the matrix 300. In this manner, the weight given to decisions made by other institutions can change with experience.

Figure 5:
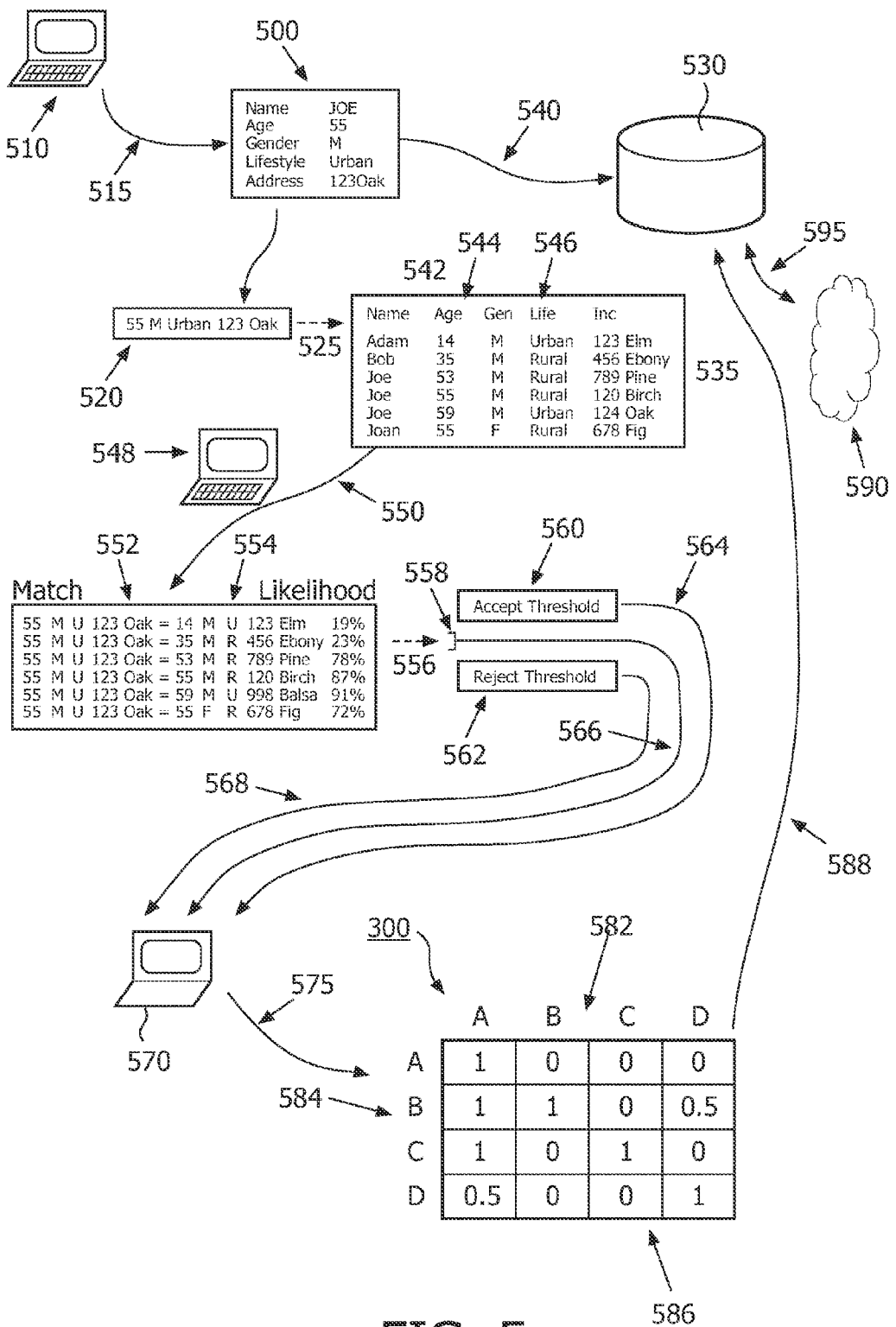
FIG. 5 illustrates how the information flows through the apparatus.

With reference to FIG. 5, the flow of information through an apparatus which may be programmed to perform the present application such as but not limited to a computer. is illustrated 500. Data is entered via an input terminal 510 and formatted 515 in a common format 500 for storage 540 in a database 530 and for comparison. The input data is exerpted in any predefined form and used to create a unique identifier 520. This input identifier is comprised of demographic data such as, but not limited to name 542, age 544, and gender, lifestyle, telephone number and address 546. The input data is used to derive a unique identifier which is used as a pointer to compare 525 with other data. The database records are retrieved 535 and compared (one record and one comparison at a time) 550 until each record in the database 530 has been compared. The database contains records previously entered and is comprised of similar types of demographic data such as, but not limited to name 542, age 544, and gender, lifestyle, telephone number, and address 546.

The format of the input data must be the same as the format of the data stored in and retrieved from the database for an accurate comparison to occur. The format depicted in FIG. 5 where age, one letter for gender, one letter for lifestyle, and several digits for address 520 is not the only format that can be used, but it must be the same format as the data in the database 535 for the matching to occur.

After each record comparison is performed, the results are processed 548 and a likelihood ratio 554 of a match existing between the input record 510 and each database record 552 is calculated for each record to which the input record 510 was compared against In one embodiment, a memory 530 contains or references a correspondence table of patient records that have been manually accepted by other institutions as matching or manually rejected as not matching and which institution (5). The memory also contains the confidence matrix 300. If a hospital with a zero confidence value in the matrix has made a manual match or rejection, the prior match or rejection is given zero weight, i.e., ignored. If a hospital with a confidence value of 1 has manually matched the input record to another record, such prior match causes a likelihood ratio of 100% to be assigned. Confidence values between 0 and 1 cause the likelihood ratio to be boosted accordingly. A prior manual rejection by another institution causes the likelihood ratio to be downgraded analogously. This likelihood ratio can also be subsequently adjusted by a chosen probabilistic formula and then compared 556 with an accept threshold 560 and a predefined reject threshold 562. Matches with a likelihood ratio greater than the accept threshold are asserted to be a match 564, and matches with a likelihood ratio below the reject threshold are asserted to be rejected 568. Records that have a likelihood ratio less than the accept threshold 560 and higher than the reject ratio 562 are flagged for manual review 566.

After a manual review is performed, the result is input 570. Then each of the assertions for each pair of comparisons is broken down by receiving institution 575 and averaged to calculate a percentage of input records received 586, which is placed in the matrix 300. The matrix contains the names of the institution submitting, supplying, or transmitting a record on one axis and the institution receiving the record on the other axis. The horizontal axis 582 may be for the sending or receiving institution while the vertical axis 584 may receive either the sending or receiving institution.

The matrix is then recorded 588 in a database 530 and may be shared among other institutions who are either members or are not members of the federation of institutions via a network such as but not limited to the Internet 590 by way of an Internet connection 590.

For example, the entered record is for Joe, a 55 year old male urban dweller. A comparison with a record in the database of Adam, a 14 year old male urban dweller would produce a low 19% likelihood ratio of a match due to the great age and address disparity between the two compared records. If the threshold ratio of rejection were 20%, then this record with a 19% ratio would fall below the 20% rejection threshold and would be rejected. These two compared records are probably not for the same person.

Another comparison, this time of the entered record of Joe the 55 year old male urban dweller with the database record of another different Joe who is 59 years old, a male urban dweller would produce a higher likelihood ratio of 91% because these two records are a much closer match in terms of age and address. If the threshold ratio for accept were 90%, then this record with an acceptance ratio of 91% would be above the 90% acceptance ratio and would be accepted as a match. These two compared records are likely for the same person.

A comparison with a record for Joan, a 55 year old female rural dweller would produce a likelihood ratio of 72%. As this 72% is above the 20% reject ratio and also below the 90% accept ratio, this record would be placed on an exception list and flagged for manual review. Only a manual review could determine whether these records are for the same person.

Each demographic factor can be, but is not necessarily, equally weighted. For example, an individual's address can change a great deal in a short period of time. Therefore this demographic might be weighted to be of less importance than other demographics. A demographic that rarely or never changes, such as gender or race, might be given greater weight because this demographic may be more reliable as an indicator of a specific person. This could explain why the likelihood match between Joe 55 M U 123 Oak and Joe 59 M U 998 Balsa is at 91% despite the great difference in addresses between these two individuals. Here, the similarity in age, gender, and lifestyle is weighted more heavily than address is weighted.

In another embodiment, prior match and rejection determinations and the institution making such determination is provided to the manual reviewer. The manual reviewer is also provided with the institution confidence matrix 300. The manual review weights the prior decisions in accordance with the confidence value accorded to the other hospital.

In another embodiment, the prior match/reject decisions and the confidence matrix 300 can be used to adjust the accept or reject thresholds.

When two institutions make contrary decisions on whether two records match, a conflict notice is sent to both institutions. The two records can be automatically sent to the manual reviewers at both institutions for reconsideration.

The above-described process is performed on one or more computers or computer systems with one or more computer software programs. Computer programs for performing the steps can be stored on a tangible computer readable medium, such as a disc, computer memory, or the like.

The present disclosure has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A method of reusing comparisons, comprising:
  at a first medical institution:
    (a) receiving a record supplied by an at least one second medical institution with an input;
    (b) comparing the received record with a plurality of records currently maintained by a receiving party in order to determine if any two compared records correspond to a same customer with at least one computer processor;
    (c) generating a likelihood ratio based on a probability value that the compared records match with the at least one computer processor;
    (d) comparing the likelihood ratio to an accept threshold and to a reject threshold, the accept threshold being different from the reject threshold with the at least one computer processor;
    (e) assigning a record to an exception list stored in a central database when the record's likelihood ratio is both less than the accept threshold and is also greater than the reject threshold to an exception list with the at least one computer processor;
    (f) determining whether the records on the exception list should be accepted as a match or rejected as not matching and recording the determination with the at least one computer processor;
    (g) receiving assertions made by the at least one second medical institution indicative of whether records on the exception list were accepted or rejected as matching with the at least one computer processor;
    (h) comparing the records on the exception list that were at least one of accepted and rejected by both the first medical institution and each of the at least one second medical institution in order to calculate an assertion acceptance value for each outside party with the at least one computer processor; and
  at the central database:
    (i) creating a matrix of assertion acceptance values by:
      placing the name of at least one party which receives assertions on one axis with the at least one computer processor,.
      placing the name of at least one party which issues the assertions on a second axis with the at least one computer processor: and
      creating one cell for each intersection between the receiving axis and the issuing axis, wherein each cell contains at least one assertion acceptance value with the at least one computer processor;
    (j) recording the assertion acceptance values in the matrix with the at least one computer processor for access by a federation of a plurality of medical institutions, the records being patient records of a federation of medical institutions, the institutions having different medical records systems, some patients having unmatched patient records in the medical systems of a plurality of the medical institutions; and (k) at at least a third medical institution, retrieving the assertion acceptance value matrix from the database and utilizing the assertion acceptance value matrix to automatically accept or reject records on the exception list.

2. The method of claim 1, where the probability value is within the in the range from 0 to 1 inclusive, where 0 represents no acceptance and 1 means the received assertion is the ground truth.

3. The method according to claim 1, wherein each assertion acceptance value is calculated as a weighted ratio of prior common assertions determined by the receiving party and each other party.

4. The method according to claim 1, wherein each cell in the matrix of assertion acceptance values may contain separate assertion acceptance values for a positive assertion and one for a negative assertion.

5. The method according to claim 1, wherein the first medical institution, the at least one second medical institution, and the at least one third medical institution are members of a common federation of medical institutions and the records are patient records, the institutions having different medical record systems with different patient identifiers.

6. The method according to claim 5, wherein the received record and an accepted record of one of the medical institutions in the federation of plurality of medical institutions are assigned a unique, federation wide medical record number.

7. The method according to claim 1, wherein the acceptance value matrix is at least one of:
used in the likelihood ratio generating step to increase or decrease the probability in accordance with the acceptance values; or
used in the step of determining whether records on the exception list should be accepted or rejected.

8. A non-transitory computer readable medium programmed with software which when implemented by a processor performs the method according to claim 1.

9. An assertion acceptance value matrix stored on a non-transitory computer readable medium generated by the method according to claim 1.

10. The method according to claim 1, further including:
performing (a)-(k) at at least one other medical institution of the federation of a plurality of medical institutions.

11. An apparatus for generating reusable comparisons, comprising:
an input of a first medical institution which receives records supplied by at least one second medical institution, the records being patient records of a federation of medical institutions including the first and the at least one second medical institution, the institutions having different medical records systems, some patients having unmatched patient records in the medical systems of a plurality of the medical institutions;
a database which stores a plurality of records;
at least one computer processor which:
(a) compares the received record with each record retrieved from the database in order to generate a likelihood ratio based on a probability that the compared records match;
(b) compares the likelihood ratio to both an accept threshold and a reject threshold,
(c) assigns a record that is between the accept threshold and the reject threshold stored in the database to an exception list for a manual determination whether the records on the exception list match;

wherein the at least one processor further:
(d) receives assertions made by the at least one second medical institution wherein the assertion comprises whether the records on the exception list were accepted or rejected as matching;
(e) compares the records on the exception list that were at least one of accepted and rejected both by the first medical institution and each of the other medical institutions in the federation in order to calculate an assertion acceptance value for each medical institution,
(f) creating a matrix of assertion acceptance values including at least one receiving axis representing the first medical institution, an issuing axis representing the at least one second medical institution. one cell for each intersection between the receiving axis and the issuing axis, wherein each cell contains at least one acceptance value; and
(g) records the assertion acceptance values in the matrix for access by a federation of a plurality of medical institutions, the records being patient records of a federation of medical institutions, the institutions having different medical records systems, some patients having unmatched patient records in the medical systems of a plurality of the medical institutions; and
wherein, at at least a third medical institution, the assertion acceptance value matrix is retrieved from the database and utilized to automaticall accept or reject records on the exception list.

12. The apparatus according to claim 11, wherein the matrix is accessible by each medical institution in the federation of medical institutions.

13. The apparatus according to claim 1 1, wherein each cell in the matrix contains separate assertion acceptance values for a positive assertion and for a negative assertion.

14. The apparatus according to claim 11, wherein the at least one computer processor is further programmed to :
perform (a)-(g) at at least one other medical institution of the federation of a plurality of medical institutions.

15. A method of matching patient records for a plurality of medical institutions with different medical records systems, with some patients having records in a plurality of the medical records systems, the method comprising:
(a) comparing a selected patient medical record in a medical records system of a first medical institution with a plurality of patient records from at least one other medical institution having a corresponding medical record system with at least one computer processor;
(b) generating likelihood ratios indicative of a probability that the selected patient medical record matches each of the compared records with the at least one computer processor;
(c) automatically (1) matching the selected patient medical record with one of the compared records if the likelihood ratio exceeds an accept threshold, (2) not matching the selected patient medical record with compared records that meet a reject threshold, and (3) if the selected patient medical record and one or more compared records do not meet either the accept or the reject threshold, assigning the selected patient medical record to an exception list for manual review in a database with the at least one computer processor;
(d) receiving an indication whether the selected patient medical record was matched to one of the compared records by at least one other of the medical institutions with a corresponding input;

(e) performing at least one of the manual review and the generating step in accordance with an assertion acceptance value matrix indicative of a reliability of matches made by other medical institutions with the at least one computer processor the matrix of assertion acceptance values being created by:

placing the name of at least one other medical institutions which receives assertions on one axis with the at least one computer processor;

placing the name of at least one other medical institutions which issues the assertions on a second axis with the at least one computer processor; and creating one cell for each intersection between the receiving axis and the issuing axis, wherein each cell contains at least one assertion acceptance value with the at least one computer processor;

(f) storing the created matrix in the database for access by a federation of a plurality of medical institutions including the first and at least one second medical institution, the records being patient records of the federation of medical institutions, the institutions having different medical records systems, some patients having unmatched patient records in the medical systems of the plurality of the medical institutions;

(g) utilizing the acceptance value matrix at at least one other medical institution of the federation of medical institutions other than the first and the at least one second institutions to automatically accept or reject records on the exception list.

16. The method according to claim 15, wherein each assertion acceptance value is calculated as a weighted ratio of prior common assertions determined by the receiving party and each other party.

17. The method according to claim 15, wherein each cell in the matrix of assertion acceptance values may contain separate assertion acceptance values for a positive assertion and one for a negative assertion.

18. The method according to claim 15, wherein the acceptance value matrix is utilized to adjust the accept and reject thresholds.

19. The method according to claim 15, further including:

performing (a)-(g) at at least one other medical institution of the federation of a plurality of medical institutions.

* * * * *